(12) United States Patent
Ormsby et al.

(10) Patent No.: US 8,115,050 B2
(45) Date of Patent: Feb. 14, 2012

(54) SOAKER PAD FOR CLOTH DIAPER

(75) Inventors: Kim Ormsby, Bozeman, MT (US);
Allen Leo, Nanjing (CN)

(73) Assignee: The Natural Baby Company, LLC,
Bozeman, MT (US)

( * ) Notice: Subject to any disclaimer, the term of this patent is extended or adjusted under 35 U.S.C. 154(b) by 221 days.

(21) Appl. No.: 12/632,791

(22) Filed: Dec. 7, 2009

(65) Prior Publication Data

US 2011/0137278 A1    Jun. 9, 2011

(51) Int. Cl.
*A61F 13/15* (2006.01)
*A61F 13/20* (2006.01)

(52) U.S. Cl. .................................. 604/358; 604/385.27

(58) Field of Classification Search .................. 604/358, 604/385.14–385.15, 385.01, 397–402
See application file for complete search history.

(56) References Cited

U.S. PATENT DOCUMENTS

| | | | |
|---|---|---|---|
| 2,649,858 A | | 8/1953 | Le Bolt |
| 3,903,889 A | | 9/1975 | Torr |
| 4,695,278 A | | 9/1987 | Lawson |
| 5,019,072 A | | 5/1991 | Polski |
| 5,071,415 A | | 12/1991 | Takemoto |
| 5,137,526 A | * | 8/1992 | Coates ........................ 604/391 |
| 5,185,009 A | | 2/1993 | Sitnam |
| 5,350,370 A | | 9/1994 | Jackson et al. |
| 5,374,259 A | | 12/1994 | Takahashi et al. |
| 5,405,342 A | * | 4/1995 | Roessler et al. ............. 604/364 |
| 5,542,940 A | | 8/1996 | Jonker |
| 5,613,959 A | | 3/1997 | Roessler et al. |
| 5,707,364 A | * | 1/1998 | Coates ........................ 604/391 |
| 6,258,076 B1 | | 7/2001 | Glaug et al. |
| 6,277,106 B1 | | 8/2001 | Boudry et al. |
| 6,394,990 B1 | | 5/2002 | Rosenfeld et al. |
| 6,491,677 B1 | | 12/2002 | Glaug et al. |
| 6,524,289 B1 | | 2/2003 | Larsson et al. |
| 6,531,642 B2 | | 3/2003 | Kurata et al. |
| 6,616,649 B1 | | 9/2003 | Ismail |
| 6,680,423 B1 | | 1/2004 | Tanzer |
| 7,118,557 B2 | | 10/2006 | Minato et al. |
| 7,381,203 B2 | | 6/2008 | Kasai |
| 2002/0013560 A1 | | 1/2002 | Erspamer et al. |
| 2003/0225383 A1 | | 12/2003 | Glaug et al. |
| 2005/0222545 A1 | | 10/2005 | Flores Gonzales |
| 2006/0184151 A1 | | 8/2006 | Onishi et al. |
| 2006/0247589 A1 | | 11/2006 | Seneviratne |
| 2007/0208319 A1 | | 9/2007 | Minato |
| 2007/0232178 A1 | | 10/2007 | Polat et al. |
| 2007/0232180 A1 | | 10/2007 | Polat et al. |
| 2008/0058739 A1 | | 3/2008 | Roberts et al. |
| 2008/0312632 A1 | | 12/2008 | Fernfors |
| 2009/0062763 A1 | | 3/2009 | Hancock-Cooke et al. |

* cited by examiner

*Primary Examiner* — Michele M Kidwell
(74) *Attorney, Agent, or Firm* — Antoinette M. Tease

(57) ABSTRACT

A soaker pad for a cloth diaper comprising an outer layer, absorbent pad, inner layer, and side panels. The inner longitudinal edge of each side panel is folded inward to create a fold line and fold area. Elastics are located just inside the fold line to create an inner gusset. Elastics are situated parallel to the longitudinal edge of the outer layer to create an outer gusset. Neither the inner nor outer gusset is in contact with the inner layer. Each side panel is adhered to the outer layer in the margin along each longitudinal edge of the outer layer that is not in contact with the inner layer and along the outer margins of the inner layer. The fold area is adhered to the inner layer except at the middle portion of the fold area, thereby allowing the inner gusset to stand up and away from the inner layer.

4 Claims, 4 Drawing Sheets

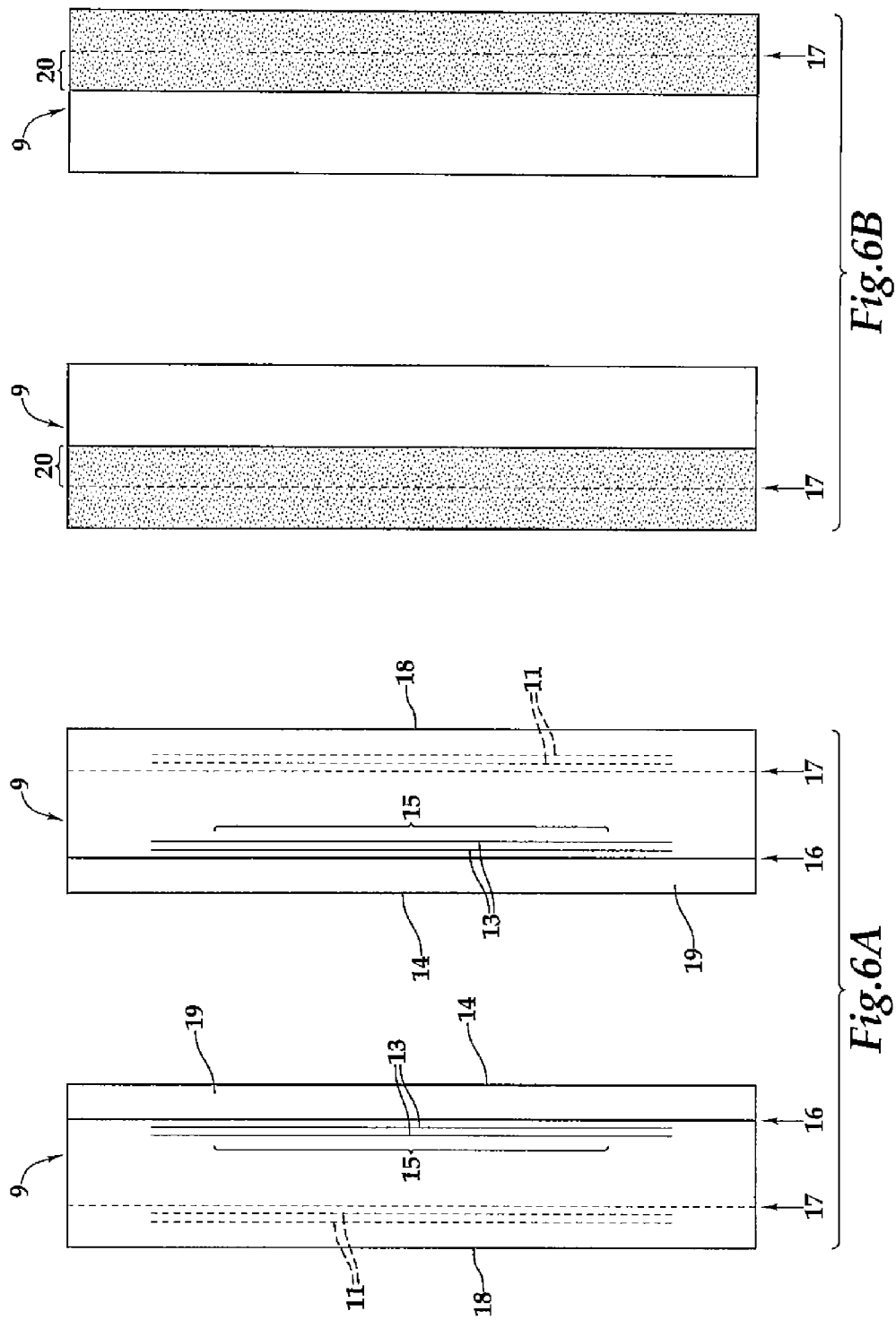

SOAKER PAD FOR CLOTH DIAPER

BACKGROUND OF THE INVENTION

1. Field of the Invention

The present invention relates generally to the field of diapers, and more specifically, to a soaker pad for use with a cloth diaper.

2. Description of the Related Art

Cloth diapers are presently widely used as an alternative to non-biodegradable disposable diapers because they are generally considered to be environmentally friendly. Cloth diapers pose their own challenges, however, including designing a soaker pad for insertion into the cloth diaper that will fit a baby snugly so as to minimize any soiling of the cloth diaper itself. An ideal soaker pad would incorporate an outer waterproof layer so as to further prevent the waste inside the soaker pad from coming into contact with the diaper. In addition, the soaker pad should be easy to install and remove. Preferably, the soaker pad would be biodegradable.

There have been a number of diaper innovations over the years, none of which incorporates the unique design features of the present invention. For example, U.S. Pat. No. 3,903,889 (Torr, 1975) describes a multi-layer, disposable absorbent product with a liquid-pervious inner layer, a liquid-impervious outer layer, a liquid-absorbent organic material between the inner and outer layers, and a bulking material between the inner and outer layers. Two films of a water-repellent adhesive agent surround the absorbent organic material.

U.S. Pat. No. 5,185,009 (Sitnam, 1993) provides a biodegradable diaper with an outer sheet of biodegradable material that resists water absorption, an inner sheet of biodegradable material that allows liquid to pass through it, and an absorbent core between the inner and outer layers. A water-resistant film of biodegradable material within the core assists in fluid distribution.

U.S. Pat. No. 5,350,370 (Jackson et al., 1994) describes a high-wicking and liquid-absorbent composite made from a relatively uniform mixture of specified percentages of fine wettable fiber, pulp fibers, superabsorbent and binder. The mixture is compressed to a specified density and vertical wicking height. To make the composite, a sheet is formed of fine wettable fiber and pulp fiber, and then that sheet is fiberized into a plurality of individual fibers within an air stream. A superabsorbent is then mixed with the fibers from the fiberized sheet in the air stream to form a uniform mixture, which is deposited onto a forming surface to form the composite. After the composite it formed, it is compressed to the desired density.

U.S. Pat. No. 5,374,259 (Takahashi et al., 1994) discloses a biodegradable diaper comprising a liquid absorbing material, a liquid permeable surface material, and a leak-proof backing material. The liquid permeable material is formed of either an aliphatic polyester resin obtained by reacting an aliphatic saturated polyester prepolymer having an end group that is materially a hydroxyl group with a coupling agent or an aliphatic polyester resin and an aliphatic saturated polyester resin that has not been treated by the coupling agent.

U.S. Pat. No. 5,542,940 (Jonker, 1996) provides a disposable diaper comprising a liquid permeable bodyside inner liner and a substantially liquid impermeable outer layer. A liquid-absorbent batt is situated between the inner liner and the outer layer. The diaper comprises elastic leg openings. The inner liner and outer layer are made of a cellulosic material of the "wet-strong long fiber" type.

U.S. Pat. No. 6,531,642 (Kurata et al., 2003) describes a water-decomposable absorbent article with a water-decomposable back layer, a water-decomposable and liquid-pervious surface layer, and a water-decomposable absorbent layer in between the back layer and the surface layer. The back and surface layers are bonded to each other along an outer peripheral region. A thermoplastic water-soluble adhesive is applied in a strip shape between the back layer and the surface layer in a predetermined width along the peripheral edge in the outer peripheral region. The back and surface layers are heat-sealed with the thermoplastic water-soluble adhesive disposed between the two layers in the outer peripheral region.

U.S. Pat. No. 6,680,423 (Tanzer, 2004) discloses an absorbent elastic nonwoven composite material with stretch properties. The composite has an elastic filament matrix that is reinforced with bond lines that run transversely to the machine direction of the composite material. The elastic filament matrix contains a plurality of elastomeric nonwoven filaments, absorbent fibers and a superabsorbent material. The bond lines prevent separation of the elastic nonwoven filaments, the absorbent fibers and the superabsorbent material during stretching and improve elastic recovery of the composite material.

U.S. Pat. No. 7,166,094 (Glaug et al. 2007) provides an absorbent article with a fluid-permeable body-facing surface and an absorbent core with a body-facing side. An absorbent pledget is situated between the absorbent core and the body-facing surface and is adhered to the body-facing side of the absorbent core. The pledge has a greater structural stiffness and a reduced surface area as compared to the absorbent core.

Other examples of technologies relating to diapers and/or absorbent materials include U.S. Patent Application Pub. No. 2002/0013560 (Erspamer et al.) (absorbent structure with integral vapor transmissive moisture barrier); U.S. Patent Application Pub. No. 2005/0222545 (Gozales) (biodegradable pants diaper); U.S. Patent Application Pub. No. 2006/0247589 (Seneviratne) (multi-layered composition comprising an outer cover of natural fabric and cotton felt and an absorbent core having a top layer of a natural feather fabric and a lower layer of a waterproof coating of wax, the absorbent core optionally comprising natural fluffed pulp and gel); U.S. Patent Application Pub. Nos. 2007/0232178 and 2007/0232180 (Polat et al.) (method for forming a nonwoven fibrous structure comprising a plurality of synthetic fibers associated with one or more hydrophilizing agents and absorbent article comprising same); and U.S. Patent Application Pub. No. 2008/0058739 (Roberts et al.) (absorbent article with a liquid-pervious top sheet, a liquid-impervious back sheet, and an absorbent core including expanded starch particles).

The present invention has a unique double-gusset design in the area of the leg enclosures. Although the following patents deal with leg gussets, none of these gusset designs is structured as in the present invention: U.S. Pat. No. 4,695,278 (Lawson, 1987) (gasketing cuff or outer gusset is simply an elastic region created in the topsheet itself; barrier cuff or inner gusset is a separate element secured to the topsheet); U.S. Pat. No. 7,118,557 (Minato et al., 2006) (comprising only two barrier cuffs); U.S. Pat. No. 7,381,203 (Kasai, 2008) (outer leg gathers formed by elastic members between the backsheet and standing gather-forming sheets on either side of the diaper; inner standing gathers formed by fixing standing gather-forming sheets to the topsheet at a joint). Additional examples of diapers with gusset designs include U.S. Patent Application Pub. No. 2006/0184151 (Onishi et al.); U.S. Patent Application Pub. No. 2007/0208319 (Minato);

U.S. Patent Application Pub. No. 2008/0312632 (Fernfors); and U.S. Patent Application Pub. No. 2009/0062763 (Hancock-Cooke et al.).

BRIEF SUMMARY OF THE INVENTION

The present invention is a soaker pad for a cloth diaper comprising: an outer layer having two longitudinal edges, a top edge, a bottom edge and a center; an absorbent pad; an inner layer having a top edge, a bottom edge, a center and two outer longitudinal margins; and two side panels, each of which has an outer longitudinal edge, an inner longitudinal edge, a top edge and a bottom edge; wherein the absorbent pad lies between the inner and outer layers and is situated roughly in the center of both the outer and inner layers; wherein the top and bottom edges of the inner layer are lined up with the top and bottom edges of the outer layer, and the inner layer is narrower than the outer layer, thereby forming a margin along each longitudinal edge of the outer layer that is not in contact with the inner layer; wherein the top and bottom edges of each side panel are lined up with the top and bottom edges of the outer layer, the outer longitudinal edge of one side panel is lined up with one of the longitudinal edges of the outer layer, and the outer longitudinal edge of the other side panel is lined up with the other longitudinal edge of the outer layer; wherein the inner longitudinal edge of each side panel is folded inward to create a fold line and a fold area with a middle portion, and wherein two parallel elastics are located just inside the fold line of each side panel to create an inner gusset; wherein two parallel elastics are situated parallel to the longitudinal edge of the outer layer in the margin along each longitudinal edge of the outer layer that is not in contact with the inner layer, and wherein said elastics create an outer gusset; wherein neither the inner gusset nor the outer gusset is in contact with the inner layer; and wherein each side panel is adhered to the outer layer in the margin along each longitudinal edge of the outer layer that is not in contact with the inner layer, each side panel is adhered to the outer margins of the inner layer, and the fold area of each side panel is adhered to the inner layer except at the middle portion of the fold area, thereby allowing the inner gusset to stand up and away from the inner layer.

In a preferred embodiment, the invention further comprises adhesive areas on the outer surface of the outer layer, the adhesive areas are located adjacent to the top and bottom edges of the outer layer, and the adhesive areas are covered by removable tabs. Preferably, the outer layer, absorbent pad and inner layer are all biodegradable and/or compostable.

BRIEF DESCRIPTION OF THE DRAWINGS

FIG. 6A is a plan view of the side panels of the present invention.

FIG. 6B is a plan view of the side panels of the present invention with shading to indicate where the side panel is adhered to the inner and outer layers of the soaker pad.

REFERENCE NUMBERS

Figure 1:
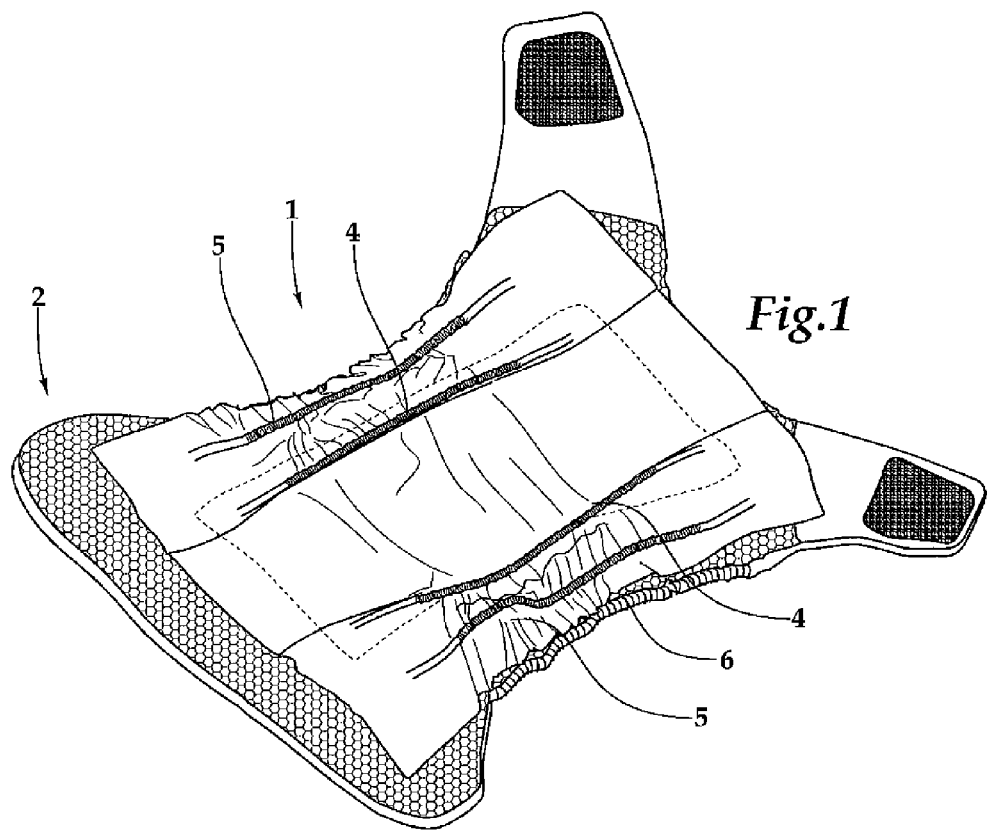
FIG. 1 is a perspective view of the soaker pad of the present invention inside of a cloth diaper.

1 Soaker pad
2 Cloth diaper
3 Removable tab
4 Inner gusset
5 Outer gusset
6 Outer elastic section (of cloth diaper)
7 Outer layer
8 Inner layer
9 Side panel
10 Absorbent pad
11 Elastics (of outer gusset)
12 Longitudinal edge (of outer layer)
13 Elastics (of inner gusset)
14 Inner longitudinal edge (of side panel)
15 Area where inner gussets stand up and away from inner layer
16 Fold line (in side panel)
17 Point (in side panel) to which inner layer extends
18 Outer longitudinal edge (of side panel)
19 Fold portion (of side panel)
20 Outer margin (of inner layer)

DETAILED DESCRIPTION OF INVENTION

FIG. 1 is a perspective view of the soaker pad of the present invention inside of a cloth diaper. The soaker pad 1 is preferably adhered to the cloth diaper 2 with an adhesive that is applied directly to the outer surface of the outer layer 7 of the soaker pad 1 and covered with removable tabs 3 (see FIG. 3). The area in which the adhesive exists is roughly the same size as the area taken up by the removable tabs 3. To install the soaker pad 2 inside the cloth diaper 2, the removable tabs 3 are removed, thereby exposing the adhesive, the soaker pad is positioned inside the cloth diaper 2 as shown in FIG. 1, and pressure is applied to the soaker pad 1 in the area of the adhesive to secure it to the inside of the cloth diaper 2. To remove the soaker pad 1, simply grab the soaker pad 1 on either end and pull it up and away from the cloth diaper 2.

As shown in FIG. 1, the soaker pad itself comprises an inner gusset 4 and an outer gusset 5 on either side of the soaker pad. The details of the formation of the inner and outer gussets are discussed in connection with subsequent figures. The purpose of the inner gusset is to prevent any excrement that is inside the soaker pad from escaping the soaker pad, and the purpose of the outer gusset is to fit the soaker pad snugly around a baby's leg. As shown in this figure, the cloth diaper 2 itself also has an outer elastic section 6 that roughly corresponds to the outer gusset of the soaker pad 1.

Figure 4:
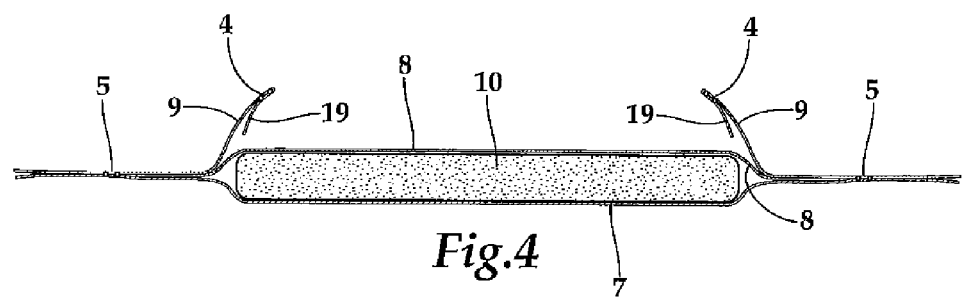
FIG. 4 is a section view of the soaker pad of the present invention taken as indicated on FIG. 2.
Figure 5:
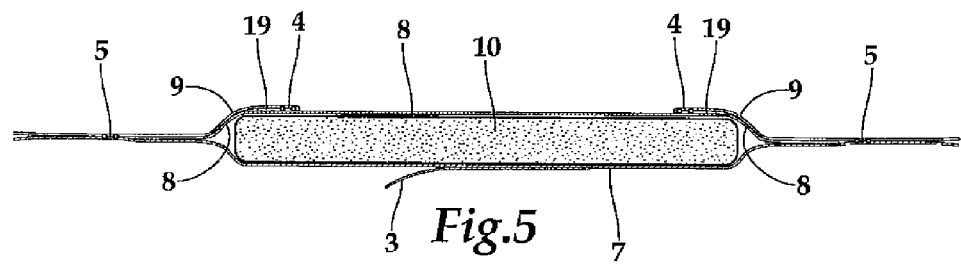
FIG. 5 is a section view of the soaker pad of the present invention taken as indicated on FIG. 2.
Figure 2:
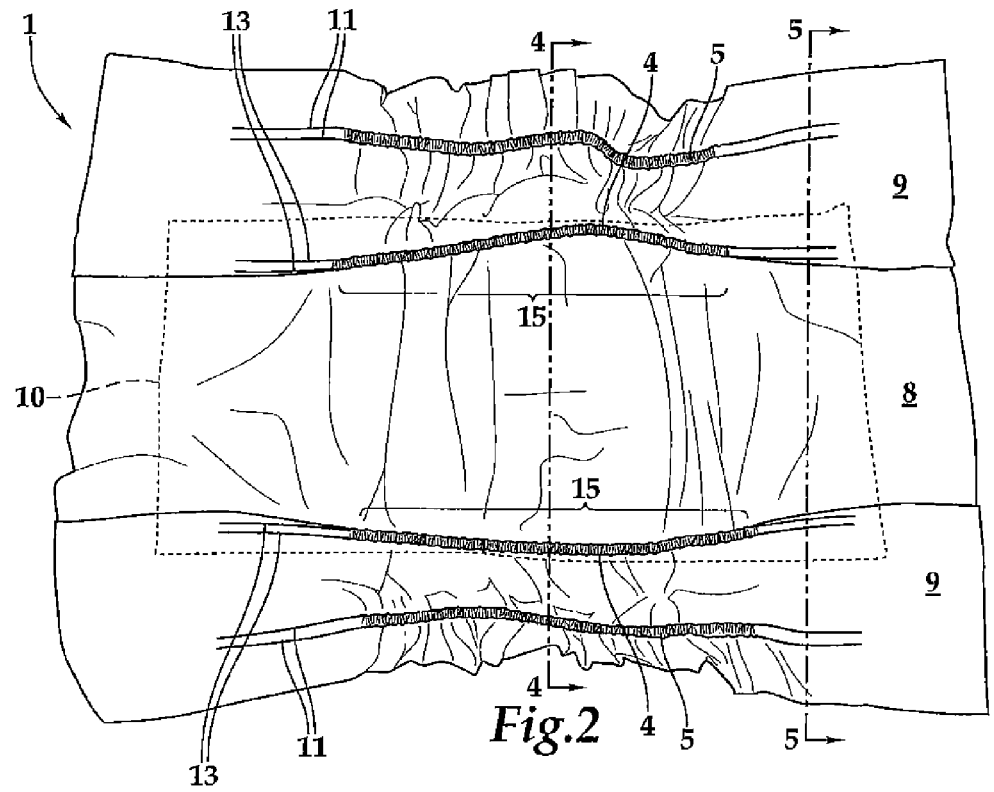
FIG. 2 is a top view of the soaker pad of the present invention.
Figure 3:
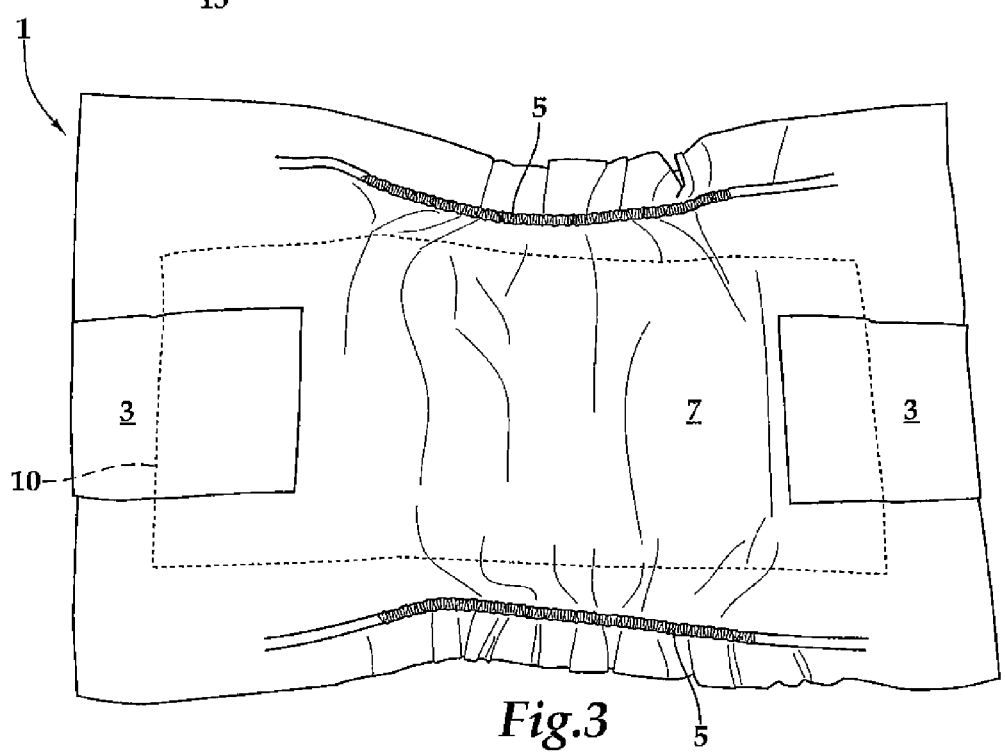
FIG. 3 is a bottom view of the soaker pad of the present invention.

FIG. 2 is a top view of the soaker pad of the present invention. This figure shows where the section views shown in FIGS. 4 and 5 are taken. FIG. 3 is a bottom view of the soaker pad of the present invention. This figure shows the removable tabs 3 that overlie the adhesive areas on the outer surface of the outer layer 7 of the soaker pad 1. As shown in FIG. 3, the inner gussets 4 are not visible from the bottom view (i.e., outer layer) of the soaker pad because the inner gussets 4 are formed from side panels 9 (see FIG. 6) that overlie the outer and inner layers 7, 8 of the soaker pad 1. The outer gussets 5, on the other hand, are formed from the outer layer 7.

FIG. 4 is a section view of the soaker pad of the present invention taken as indicated on FIG. 2. As shown in this figure, the soaker pad 1 comprises an outer layer 7, an inner layer 8, two side panels 9, and an absorbent pad 10. The outer layer 7 is preferably comprised of a fluid-impermeable material that is compostable and/or biodegradable. One example of such a material is polycaprolactone (PCL), a biodegradable polyester. The inner layer 8 is preferably comprised of a nonwoven fluid-permeable material that is compostable and/or biodegradable. One example of such a material is polylactide (PLA), a biodegradable, thermoplastic, aliphatic polyester derived from renewable resources such as corn starch. The side panels 9 are preferably comprised of the same material as the inner layer 8. The absorbent pad is preferably comprised of wooden pulp with a super-absorbent polymer (SAP) that is capable of absorbing urine. The absorbent pad is preferably compostable and/or biodegradable as well.

Figure 6:
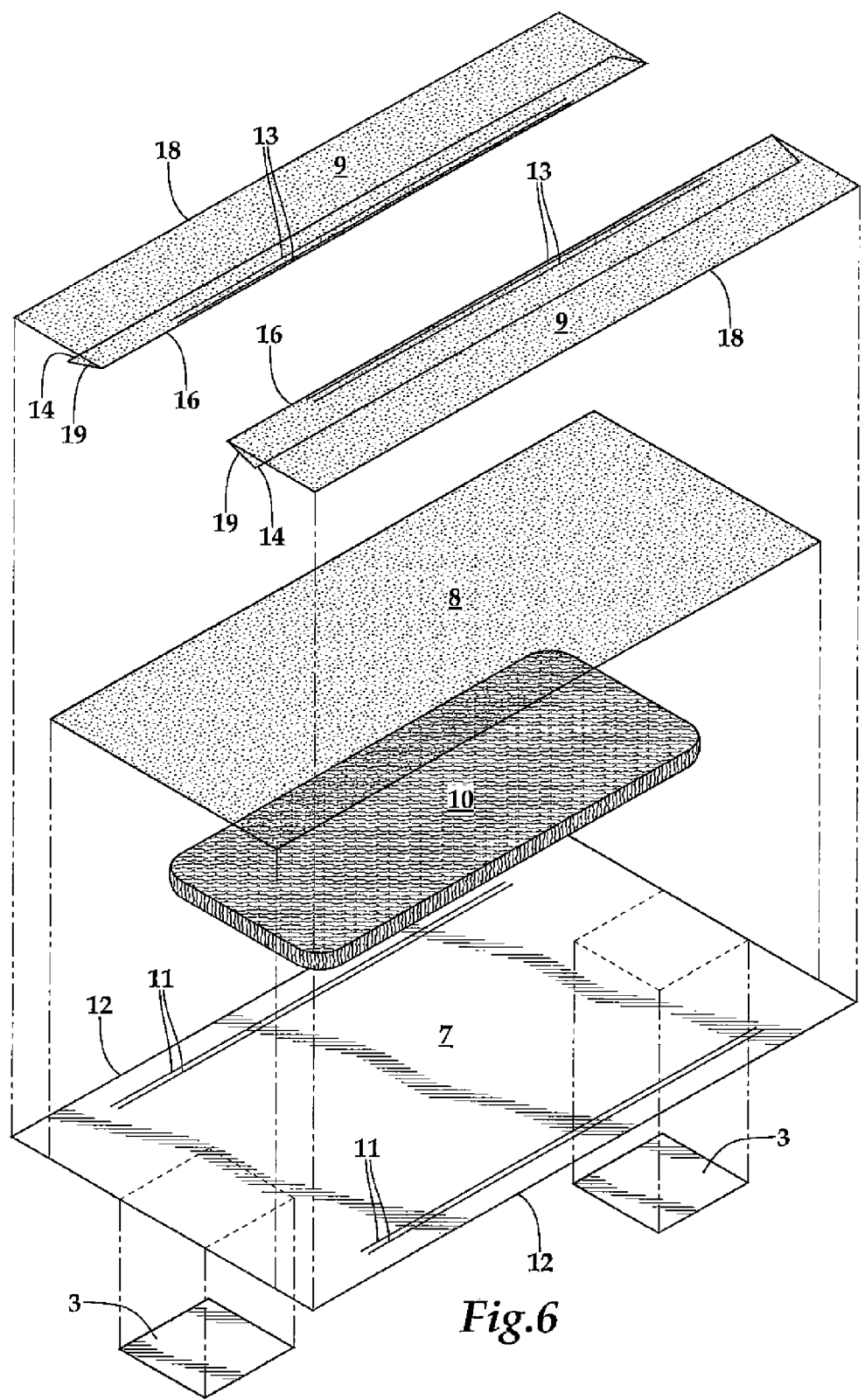
FIG. 6 is an exploded view of the soaker pad of the present invention.

The two gussets 4, 5 are formed with elastic that is preferably comprised of latex and, therefore, biodegradable. Each outer gusset 5 is preferably formed from two parallel rows of elastics 11 that are adhered directly to the outer layer 7 and parallel to the two longitudinal edges 12 (see FIG. 6) of the outer layer 7. The approximate location of these elastics is shown in FIG. 6. Each inner gusset 4 is preferably formed from two parallel rows of elastics 13 that are adhered directly to the side panel 9 and parallel to the inner longitudinal edge 14 of the side panel 9.

As shown in FIG. 4, the side panels 9 are aligned with the outer edge of the outer layer 7, and the tension in the elastics 13 causes the inner gussets 4 to stand up and away from the inner layer 8 (and absorbent pad 10) in the center area of the soaker pad 1. The area where the inner gussets 4 stand up and away from the inner layer 8 is indicated with reference number 15 on FIG. 2. Referring to FIG. 6A, reference number 16 indicates the fold line in the side panels (see also FIG. 6). Reference number 17 indicates the point to which the inner layer 8 extends when the soaker pad is assembled (it also represents the outer edge of the inner layer); as shown, the inner layer 8 does not extend as far as the outer layer 7 (which extends to the outer longitudinal edge 18 of each side panel 9), and the elastics 11 that form the outer gusset 5 do not come into contact with the inner layer 8. The fold portion 19 of each side panel is adhered to the inner layer 8 other than in area 15 (this is what allows the inner gussets 4 to stand up and away from the inner layer 8 and absorbent pad 10). In this manner, the inner gussets 4 do not come into contact with the inner layer 8 either. The side panels 9 are also adhered to the outer 7 and inner 8 layers as indicated by the shaded area in FIG. 6B.

FIG. 5 is a section view of the soaker pad of the present invention taken as indicated on FIG. 2. The difference between this figure and FIG. 4 is that the fold portion 19 of the inner gussets 4 is adhered to the inner layer 8 in FIG. 4 but not in FIG. 5.

FIG. 6 is an exploded view of the soaker pad of the present invention. As shown in this figure, the inner layer is narrower than the outer layer, and the elastics 11 that form the outer gusset 5 are situated in the outer margins of the outer layer 7 such that they do not come into contact with the inner layer 8. The absorbent pad 10 is positioned in the center of the outer layer 7, and the inner layer 8 overlies the absorbent pad 10 and is adhered to the outer layer 7 around the perimeter of the absorbent pad 10 (i.e., the inner layer 8 is adhered to the outer layer 7 everywhere other than where it overlies the absorbent pad 10). Next, the fold area 19 of the side panels 9 is adhered to the inner layer 8 except in area 15 (see FIGS. 2 and 6A), which is the location of the inner gussets 4, and the outer half of each side panel 9 is adhered to the inner and outer layers 7, 8 as indicated in FIG. 6B. As shown in FIG. 6A, area 15 is located in the middle portion of the side panel; in a preferred embodiment, it represents approximately sixty percent (60%) of the entire length of the side panel. On FIG. 6B, reference number 20 represents the outer margins of the inner layer 8 (even though technically only the side panels 9 are shown in FIG. 6B).

In a preferred embodiment, the layers are adhered together with a hot melt adhesive. One example of a suitable adhesive is DISPOMELT® adhesive manufactured by Henkel Corporation of Rocky Hill, Conn. Prior to the layers being adhered together, the elastics 11 are adhered to the outer layer 7, and the elastics 13 are adhered to the side panels 9 just inside of the fold line 16, preferably using the same adhesive as is used to adhere the layers together. In addition, this same adhesive is preferably used to form the adhesive areas underneath the removable tabs 3 on the outer surface of the outer layer 7 (see FIG. 3).

Although the preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A soaker pad for a cloth diaper comprising:
    (a) an outer layer having two longitudinal edges, a top edge, a bottom edge and a center;
    (b) an absorbent pad;
    (c) an inner layer having a top edge, a bottom edge, a center and two outer longitudinal margins; and
    (d) two side panels that are separate from the outer layer, absorbent pad and inner layer, each of which has an outer longitudinal edge, an inner longitudinal edge, a top edge and a bottom edge;
    wherein the absorbent pad lies between the inner and outer layers and is situated roughly in the center of both the outer and inner layers;
    wherein the top and bottom edges of the inner layer are lined up with the top and bottom edges of the outer layer, and the inner layer is narrower than the outer layer, thereby forming a margin along each longitudinal edge of the outer layer that is not in contact with the inner layer;
    wherein the top and bottom edges of each side panel are lined up with the top and bottom edges of the outer layer, the outer longitudinal edge of one side panel is lined up with one of the longitudinal edges of the outer layer, and the outer longitudinal edge of the other side panel is lined up with the other longitudinal edge of the outer layer;
    wherein the inner longitudinal edge of each side panel is folded inward to create a fold line and a fold area with a middle portion, and wherein two parallel elastics are located just inside the fold line of each side panel to create an inner gusset;
    wherein two parallel elastics are situated parallel to the longitudinal edge of the outer layer in the margin along each longitudinal edge of the outer layer that is not in contact with the inner layer, and wherein said elastics create an outer gusset;
    wherein neither the inner gusset nor the outer gusset is in contact with the inner layer;
    wherein each side panel is adhered to the outer layer in the margin along each longitudinal edge of the outer layer that is not in contact with the inner layer, each side panel is adhered to the outer margins of the inner layer, and the fold area of each side panel is adhered to the inner layer except at the middle portion of the fold area, thereby allowing the inner gusset to stand up and away from the inner layer; and wherein the fold area of each side panel does not come into contact with the absorbent pad.

2. The soaker pad of claim 1, further comprising adhesive areas on the outer surface of the outer layer, wherein the adhesive areas are located adjacent to the top and bottom edges of the outer layer, and wherein the adhesive areas are covered by removable tabs.

3. The soaker pad of claim 1, wherein the outer layer, absorbent pad and inner layer are all biodegradable.

4. The soaker pad of claim 1, wherein the outer layer, absorbent pad and inner layer are all compostable.

* * * * *